United States Patent [19]

Otterlei et al.

[11] Patent Number: 5,166,137
[45] Date of Patent: Nov. 24, 1992

[54] GULURONIC ACID POLYMERS AND USE OF SAME FOR INHIBITION OF CYTOKINE PRODUCTION

[75] Inventors: Marit Otterlei; Terje Espevik; Gudmund Skjåk-Bræk; Olav Smidsrød, all of Trondheim, Norway

[73] Assignees: Nobipols Forskningsstiftelse, Trondheim; Protan Biopolymer A/S, Drammen, both of Norway

[21] Appl. No.: 676,756

[22] Filed: Mar. 27, 1991

[51] Int. Cl.$^5$ .................. A61K 31/70; A61K 31/715
[52] U.S. Cl. .................................. 514/23; 514/886; 514/887; 514/921
[58] Field of Search ............... 536/3; 514/23, 886, 514/887, 921

[56] References Cited

U.S. PATENT DOCUMENTS

| | | | |
|---|---|---|---|
| 3,996,934 | 12/1976 | Zaffaroni | 424/449 |
| 4,172,120 | 10/1979 | Todd et al. | 424/43 |
| 4,382,919 | 5/1983 | Alonso et al. | 424/47 |
| 4,490,467 | 12/1984 | Jarman et al. | 435/101 |
| 4,619,913 | 10/1986 | Luck et al. | 424/484 |
| 4,663,287 | 5/1987 | Barker | 435/188 |
| 4,837,024 | 6/1989 | Michaeli | 424/446 |
| 4,950,600 | 8/1990 | Tanaka et al. | 435/182 |
| 4,990,601 | 2/1991 | Skjak-Braek et al. | 536/3 |

*Primary Examiner*—Ronald W. Griffin
*Attorney, Agent, or Firm*—Blakely, Sokoloff, Taylor, Zafman

[57] ABSTRACT

A family of compounds effective in inhibiting interleukin-1 (IL-1) production, interleukin-6 (IL-6), tumor necrosis factor (TNF) production, and the production of other leukocyte derived cytokines is comprised of oligomers and polymers of $\alpha$1-4 linked L-guluronic acid residues which may be administered to a human or mammal in an amount sufficient to inhibit the production effect of leukocyte-derived cytokines. The inhibition of IL-1, IL-6 and TNF, and other cytokines in mammals is implicated in alleviation of a wide variety of disease conditions.

11 Claims, 6 Drawing Sheets

POLY-M

M-BLOCKS

C60XY

CHITOSAN

G-BLOCKS

GULURONIC ACID POLYMERS AND USE OF SAME FOR INHIBITION OF CYTOKINE PRODUCTION

BACKGROUND OF THE INVENTION

1. Field of the Invention

This invention relates to the fields of biochemistry and immunology, and to biological materials for the suppression of immunological reactions. More specifically, this invention relates to the inhibition of the production of leukocyte derived cytokines, such as interleukin-1 (IL-1), interleukin-6 (IL-6) and tumor necrosis factor (TNF) in humans and mammals. Additionally, this invention relates to a method of inhibiting the production of cytokines to arrest or alleviate certain disease and inflammatory states.

2. Art Background

The lymphocytes or white blood cells in the animal body come in two types, B-cells and T-cells. The B-cells produce antibodies in the form of immunoglobulins that bind onto invading organisms while the T-cells produce the lymphokines or cytokines which are responsible for turning B-cells on and off.

Phagocytes important in immunology are polymorphonuclear leukocytes (e.g. neutrophils) and mononuclear phagocytes (e.g. monocytes and macrophages). Phagocyte hypofunction is a cause of recurrent pyogenic infection. To combat pyogenic infection, neutrophils and monocytes respond to chemotactic factors by moving toward the source of infection, where they ingest microorganisms and kill them.

More particularly, a main function of polymorphonuclear leukocytes and monocyte is to kill bacteria and other infectious agents by phagocytosis. The first stage in the ingestion and digestion of a particulate substance by these cells involves the process of bringing the cells and the particles together, usually through chemotaxis. This response is an essential part of host defense against infection. The extensive migration and activity of these cell is manifested by inflammation at the site of injury or invasion of the host.

It is well known that the growth of normal lymphocytes is dependent not only on contact with an antigenic substance or a mitogen, but also on the presence of certain factors known as lymphokines or cytokines.

The known types of lymphokines include IL-2, B-cell factors, macrophage activation factor (MAF), Interleukin-1 (IL-1), Interleukin-2 (IL-2), Interleukin-3 (IL-3), Interleukin-6 (IL-6), Colony Stimulating Factor (CSF), Tumor Necrosis Factor (TNF), and Gamma Interferon. All of these factors are secreted by white blood cells and are collectively known as cytokines.

Monocytes can be stimulated by various agents, such as LPS (lipopolysaccharides), to produce certain cytokines including TNF, IL-1 and IL-6. LPS contains a polysaccharide and a lipid A part. Polysaccharides such as $\beta$1-3 glucans and blocks of $\beta$1-4 D-mannuronic acid have been reported to stimulate monocytes to produce cytokines. Certain cytokine stimulating materials are described in our copending patent application, Ser. No. 07/676,102, filed Mar. 27, 1991 entitled DIEQUATORIALLY BOUND $\beta$-1,4 POLYURONATES AND USE OF SAME FOR CYTOKINE STIMULATION.

The present invention relates generally to mammalian cytokines, and particularly to the inhibition of production of biologically active mammalian IL-1, IL-6 and TNF. Interleukin-1 is the designation given to a family of polypeptides, released by macrophages and certain other cell types in response to immunogenic and traumatic stimulation, which have a primary role in initiating host response to injury and infection. These cytokines have been associated with a complex spectrum of biological activities. Specifically, IL-1 is a primary immunostimulatory signal capable of inducing thymocyte proliferation via induction of Interleukin-2 release, and of stimulating proliferation and maturation of B lymphocytes. In addition, IL-1 has been linked with prostaglandin production, induction of fever, inflammatory conditions and promotion of wound healing. Recently, both IL-1 and IL-6 have been implicated as important mediators of septic shock (Ohlsson et al., Nature 348, 550–557, 1990; Starnes et al., J. Immunol. 145, 4185–4191, 1990).

Among other activities attributed to IL-1 and other leukocyte derived cytokines is the promotion of leukocyte adherence and the inhibition of neutrophil chemotaxis, both directly contributing to disease and inflammation syndromes.

TNF has been demonstrated to have a variety of wide ranging effects on various cells and tissues in the body during the inflammatory response. TNF has been implicated as a mediator in the pathogenesis of septic shock (Waage, A., A. Halstensen, and T. Espevik, "Association between tumor necrosis factor in serum and fatal outcome in patients with meningococcal disease", Lancet:355 (1987). Thus, the ability to selectively inhibit the production of TNF is highly desirable. Agents which can selectively inhibit the production of TNF are useful therapeutics for limiting inflammatory and degenerative diseases.

Leukocyte response to an acute inflammatory stimulus involves a complex series of events, including adherence to endothelium near the stimulus. Inhibition of cytokine production can be expected to reduce the degree of inflammation seen in conditions, such a septic shock and adult respiratory distress syndrome.

The inhibition of IL-1, IL-6, TNF, and other leukocyte derived cytokines is also of benefit in controlling, reducing, and alleviating many of these conditions, including immunostimulation which causes tissue rejection and certain autoimmune disorders, as well as inflammation. Little is known, however, about the structural requirements of compositions for optimal immunostimulation and suppression thereof. In light of the desirability of inhibiting the activity of IL-1 and TNF and the activity of other leukocyte derived cytokines and the ease with which inhibition can be detected in vitro, there exists a need in the art for inhibitors of IL-1, TNF, and other cytokines, wherein the inhibitors are acceptable for in vivo administration.

SUMMARY OF THE INVENTION

The present invention aids in fulfilling these needs in the art by identifying a class of compounds that can be successfully employed in alleviating conditions caused by, or mediated by, IL-1, IL-6 TNF, and other leukocyte derived cytokines. The compounds exhibit marked inhibition of cytokine production, even at low concentrations of the mediators as demonstrated through in vivo and in vitro tests.

More particularly, this invention provides a method of inhibiting the production of IL-1, IL-6 and TNF, and other leukocyte derived cytokines in a mammal by administering thereto α1-4 linked L-guluronic acid (sometimes referred to herein as "G-blocks")

Polymers of β1-4 linked D-mannuronic acid are very potent cytokine inducers in vitro and there are similarities between LPS, which is also a potent cytokine inducer, and β1-4 linked mannuronic acid residues with respect to stimulation of TNF-α production from monocytes. Blocks of α1-4 linked L-guluronic acid inhibited the cytokine stimulating activity by β1-4 linked D-mannuronic acid residues and LPS, but not by β1-3 linked glucan. Thus, polysaccharides, such as α1-4 linked L-guluronic acid, may be used to inhibit LPS and β1-4 linked D-mannuronic acid effects on cytokine induction.

DETAILED DESCRIPTION OF THE INVENTION

Figure 1:
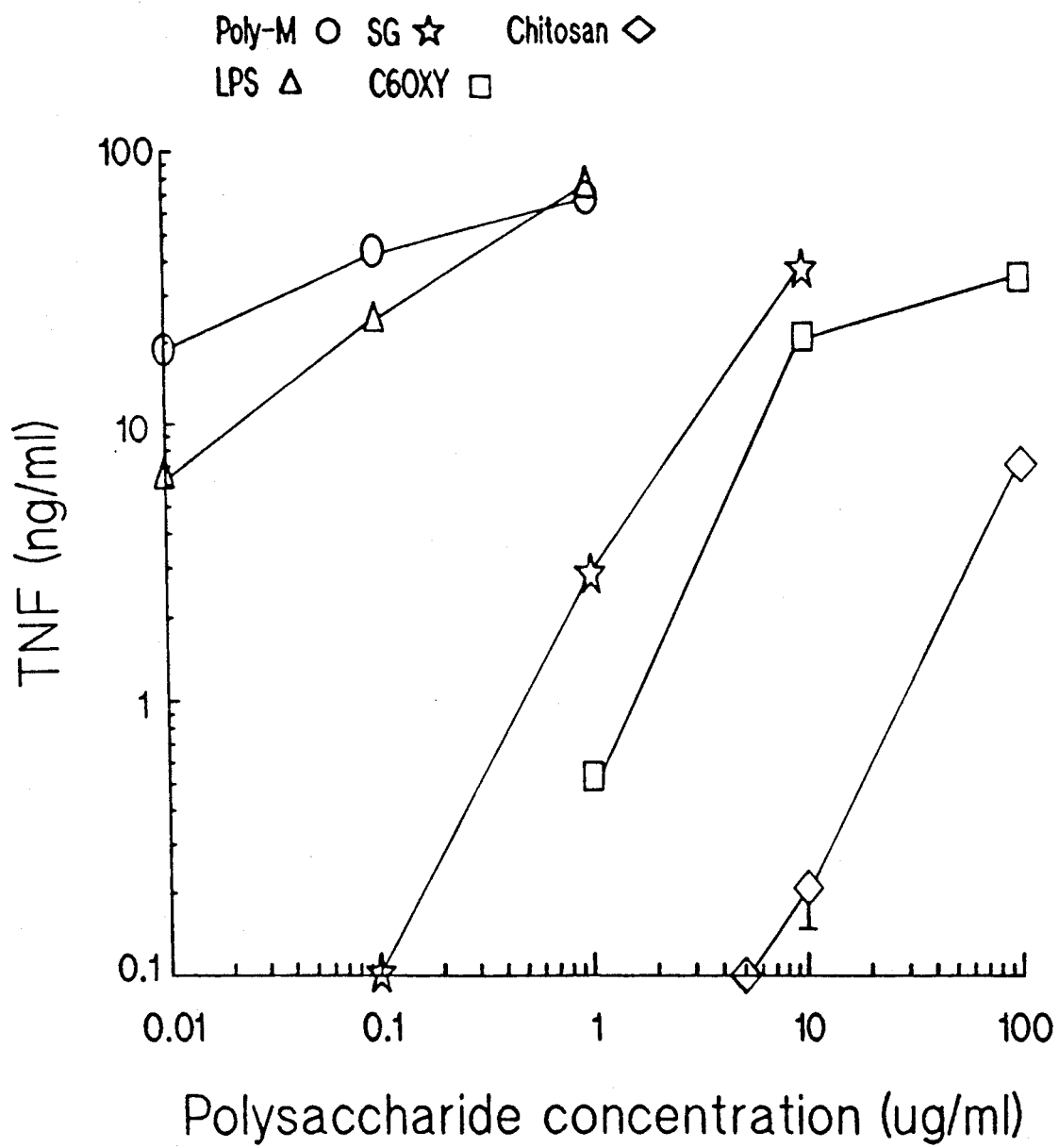
FIG. 1 is a graph showing the production of TNF-α from monocytes stimulated with poly-M (circle), LPS (triangle), SG (star), C6OXY (square) and chitosan (diamond). Production of TNF-α from unstimulated monocytes was less than 0.1 ng/ml

As used herein, the expression "leukocyte derived cytokines" is to be given a broad meaning. Specifically, the term "leukocyte" as used herein means mammalian cells of granulocytic and lymphocytic lineage. Examples of leukocytes are polymorphonuclear leukocytes, such as neutrophils, and mononuclear phagocytes, such as monocytes and macrophages and lymphocytes.

The term "cytokine" as used herein means a secretory product of a leukocyte, and in particular, a non-antibody protein released by a leukocyte on contact with antigen and which acts as an intercellular mediator of immune response. Examples of cytokines that are within the scope of this invention are chemotactic factors, factors promoting replication of lymphocytes, factors inhibiting replication of lymphocytes, factors affecting macrophage adherence, factors affecting enzyme secretion by macrophages, and factors that mediate secretion of oxidizing agents, such as oxygen, superoxide, hydrogen peroxide and hydroxyl radical.

The ability of the compounds of the present invention to inhibit the production of IL-1 and other leukocyte derived cytokines has been demonstrated and is described hereinbelow.

In summary, the compounds of the present invention employed in the process of this invention are capable of modulating the production of leukocyte derived cytokines, such as interleukin-1 and tumor necrosis factor, on phagocytes, such as polymorphonuclear leukocytes. The compounds can modulate the effects of cytokines on degranulation in stimulated phagocytes. The demonstrated inhibition of IL-1, IL-6, TNF, and other cytokines by these compounds is suggestive of clinical effectiveness in at least the certain areas and conditions discussed below.

Because IL-1, IL-6 and TNF, and other leukocyte derived cytokines have been implicated in such a wide variety of mammalian conditions, this invention has a similarly broad scope of application. Among the conditions that can be treated or alleviated by the inhibition of IL-1, IL-6, TNF production, and other leukocyte derived cytokines are: sepsis, septic shock, endotoxic shock, gram negative sepsis and toxic shock syndrome.

MATERIALS AND METHODS

Polysaccharides

The monomer composition and sequential arrangement as well as the degree of polymerization ($DP_n$) of the different polysaccharides used in the present invention were analyzed by $^1$H-n.m.r. spectroscopy on a Bruker 400 WM spectrometer as described previously by Grasdalen et al.("A p.m.r. studie of composition and sequence of uronate residues in alginate"; Carbohydr Res 1979; 68:23); (Grasdalen H. 1983. High-field $^1$H-n.m.r. spectroscopy of alginate: sequencial structure and linkage conformation. Carbohydr. Res., 118:255.)

M-blocks consisting of more than 95% D-mannuronic acid (D-ManA) were isolated from the intracellular substance of *Ascophyllum nodosum* fruiting bodies as described by Haug et al. ("Correlation between chemical structure and physical properties of alginates" *Acta chem scand* 1967:21:768). The M-blocks had a $DP_n = 30-35$.

G-blocks consisting of more than 90% L-guluronic acid (L-GulA) and with a $DP_n = 25-30$ were isolated from the algea *Laminaria diqitata* by the method described by Haug et al. ("Studies on the sequence of uronic acid residues in alginic acid" *Acta chem scand* 1967:21:691).

A high molecular weight homopolymeric β1-4 linked D-ManA (poly-M) was isolated from liquid cultures of *Pseudomonas aeruqinosa* DE 127 grown at low temperatures as described previously (Skjåk-Bræk G., Grasdalen H. and B. Larsen. 1986. Monomer sequence and acetylation pattern in some bacterial alginates. Carbohyd. Res., 154:239). The weight average molecular weight ($M_w$) was estimated from intrinsic viscosity measurement using the Mark-Howink Sakurada relation (Harding S., Vårum K. M., Stokke B. T. and O. Smidsrød. 1990. Molecular weight determination of polysaccharide. Advances in Carbohydrate Chemistry. Vol 1. JAI press., in press.). Aqueous solutions of sodium chloride (0.1M) were used at 20° C. on Ubbelohde suspended capillary viscometer with an automatic dilution viscosity system (Scott-Geräte). From this high molecular weight poly-M, samples with different chain length were prepared by partial hydrolysis for 10–120 min. at 100° C. and pH 5.4.

The β1–4 linked glucuronic acid (D-GlcA) (C60XY), prepared by oxidation of cellulose at position C-6 (Painter T. J., Cesaro A., Delben F. and S. Paoletti. 1985. New glucuronoglucan obtained by oxidation of amylose at position 6. Carbohydr. Res., 140:61), was provided by Dr. A. Cesaro, Trieste, Italy. The molecular weight ($M_w$) was estimated by viscometry to be 60,000; and the degree of oxidation (94%) was determined by potentiometric titration.

Chitin was isolated from shrimp shell and milled in a hammer mill to pass through a 0.5 mm sieve. (Hacman R. H. 1954. Studies on chitin. I. Enzymic degradation of chitin and chitin esters. Aust. J. Biol. Sci., 7:168) N-deacetylation of chitin under homogeneous conditions involved the procedure of Sannan et.al. (Sannan T., Kurita K. and. Y. Iwakura. 1976. Studies on Chitin. 2. Effect of Deacetylation on Solubility. Macromol. Chem., 177:3589). The degree of deacetylation (40%) was determined by high-field N.M.R.-spectroscopy (Vårum K. M., Anthonsen M. W., Grasdalen H. and O. Smidsrød. 1990. N.m.r. Spectroscopy of partially N-deacetylated Chitins (Chitosans). I. Determination of the Degree of N-acetylation and the Distribution of N-acetyl Groups. Carbohydr. Res., In Press). Chitosan was dissolved in acetic acid (2% w/v) by gentle shaking overnight at ambient temperature. Chitosan of different molecular weight were prepared by adding a known amount (10–100 μg) of solid $NaNO_2$, each solution was stored in the dark at room temperature overnight, and finally neutralized with NaOH. The degraded chitosans were conventionally reduced with sodiumborhydride (250 mg). The pH of the solutions were adjusted to pH 5 with HCl, the solutions were dialyzed against 0.2M NaCl and distilled water, and finally lyophilized. This converted the chitosans into the chloride salt which is readily soluble in water. The number average molecular weight ($M_n$) was determined by osmotic pressure measurements of solutions of chitosan in a Knauer Membrane Osmometer with a Sartorius SM 11736 cellulose-acetate membrane. Chitosan concentrations of 0.1–0.8% (w/v) were used.

Scleroglucan (SG), a β1-3 linked D-glucose with single β1-6 linked glycopyranose residues on every third monomer with a molecular weight of 384,000 ($M_w$), was provided by Dr. B. T. Stokke, Institute of Physichs, NTH, University of Trondheim, Trondheim, Norway.

E. coli derived LPS (Sigma) (strain 026:B6) was used in these experiments.

Endotoxin contamination in the different polysaccharides was measure by the LAL assay (Kabi vitrum, Stockholm, Sweden). The levels of endotoxin were as follows:

C60XY 1 μg contains 40 pg
1 μg of chitosan contains 1.3 pg
1 μg of SG contains 72 pg.

Monocyte cultivation

Monocytes were isolated from human A+ blood buffy coat (The Bloodbank, University of Trondheim, Norway) as described by Bøyum (Bøyum AM. 1976. Separation of monocytes and lymphocytes. Scan. J. Immunol., 5:9). Monocytes in 24 well culture plates (Costar, Cambridge, MA, USA) were cultured in complete medium consisting of RPMI 1640 (Gibco, Paisley, U. K.) with 1% glutamine, 40 μg/ml garamycin and 25% A+ serum (The Bloodbank, University of Trondheim).

The different polysaccharides and LPS were dissolved in PBS and sterile filtered through 0.2 μm filter (Nuclepore, Pleasanton, CA). The polysaccharide and LPS solutions were diluted in complete medium and added to the monocytes for 16–24 hours before the supernatants were harvested. Some monocyte cultures were preincubated with recombinant (r) human IFN-γ (rIFN-γ, Genentech, Inc. South San Francisco, CA) for 30. min. before the polysaccharides and LPS were added.

Assay for detection of TNF-α in supernatants from monocytes

TNF-α activity was determined by its cytotoxic effect on the fibrosarcoma cell line WEHI 164 clone 13, as described (Espevik T. and J. Nissen-Meyer. 1986. A highly sensitive cell line, WEHI 164 clone 13, for measuring cytotoxic factor/tumor necrosis factor from human monocytes. J. Immunol. Methods, 95:99). Dilutions of rTNF-α (rTNF-α (human) and rMuTNF-α, Genentech) were included as a standard. The TNF-α specificity of the assay was verified by using a monoclonal antibody against rTNF-α which completely neutralized the recorded activity (data not shown). Results are presented as ng/ml ± S. E. of triplicate determinations.

Assay for detection of IL-1 in supernatants from monocytes

IL-1 activity was determined by a two stage assay. The first stage involves the mouse thymocyte EL-4 NOB-1 cell line which produces high concentrations of Interleukin-2 (IL-2) in response to human IL-1, as described by Gaering et al. (Gearing A. J. H., Bird C. R., Bristow A., Poole S. and R. Thorpe. 1987. "A simple sensitive bioassay for Interleukin-1 which is unresponsive to $10^3$ U/ml of Interleukin-2." J. Immunol. Methods, 99:7). Dilutions of rIL-1β (Glaxo, Geneva Switzerland) were included as standard. After incubation in 37° C., 5% $CO_2$ atm. for 24 hours 100 ml of the supernatants were transferred into a replicate 96-well microplate. The second stage in this assay involves the IL-2 dependent mouse T cell line HT-2 as described by Mosmann, T. (Mosmann T. R., Cherwinski H., Bond M. W., Giedlin M. A. and R. L. Coffman. 1986. Two types of murine helper T cell clone. I. Definition according to profiles of lymphokine activities and secreted proteins. J. Immunol., 136:2348). One hundred μl of HT-2 suspension ($1.5 \times 10^5$ cells/ml) were added to each well and incubated for an additional 24 hours. The IL-1 activity was completely neutralized by two polyclonal antibodies against rIL-1b and rIL-1a (gift from Dr. A. Shaw, Glaxo, Geneva, Switzerland), (data not shown). Results are presented as ng/ml ± S. E. of triplicate determinations.

Assay for detection of IL-6 in supernatants from monocytes

IL-6 activity was determined by the IL-6 dependent mouse hybridoma cell line B.13.29 clone 9, as described by Aarden et al. (Aarden L. A., De Groot E. R., Schaap O. L. and P. M. Lansdorp. 1987. Production of hybridoma growth factor by monocytes. Eur. J.

Immunol., 17:1411). Dilutions of the supernatants and rIL-6 as a standard, were incubated in a 96-well microplate together with cells ($5 \times 10^4$ cells/ml) for 72 hours. (Brakenhoff J. P. J., De Groot E. R., Evers R. F., Pannekoekh H. and L. A. Aarden. 1987. Molecular cloning and expression of hybridoma growth factor in *Escherichia coli*. J. Immunol., 139:4116) The plates were harvested and the IL-6 activity was determined colorimetrically (see below). The IL-6 activity was completely neutralized by a polyclonal antibody against rIL-6 (gift from Dr. W. Fiers, University of Ghent, Belgium), (data not shown). Results are presented as ng/ml ± S. E. of triplicate determinations.

MTT-assay (3-(4,5-dimethylthiazol-2-yl)-2,5-diphenyl tetrazolium bromide)

Viability in the assays for TNF-α, IL-1 and IL-6 were measured in a colorimetric assay for growth and survival by using a tetrazolium salt as described by Mosmann (Mosmann T. 1983. Rapid colorimetric assay for cellular growth and survival: Application to proliferation and cytotoxicity assays. J. Immunol. Methods, 65:55).

RESULTS

It has previously been shown that blocks of β1–4 linked D-ManA (M-blocks) isolated from the algea *Ascophyllum nodosum* stimulated human monocytes to produce TNF-α, IL-1 and IL-6 (Otterlei M., Østgaar K., Skjåk-Braek G., Smidsrød O. and T. Espevik. 1991. Induction of cytokine production from human monocytes stimulated with alginate. J. Immunotherapy, In press). In our copending application, we disclosed the isolation of polymers of β1–4 linked D-ManA (poly-M) from *Pseudomonas aeruginosa* and compared the TNF-α inducing ability of the poly-M with other β1–4 and β1–3 linked polysaccharides. FIG. 1 shows that poly-M is approximately equally potent as LPS, around 100 times more potent than β1–3 linked D-glucose (SG), 500 times more potent than cellulose oxidized in C-6 position (C60XY) and 10,000 times more potent than chitosan in their respective abilities to induce production of the cytokines (TNF).

Figure 4C:
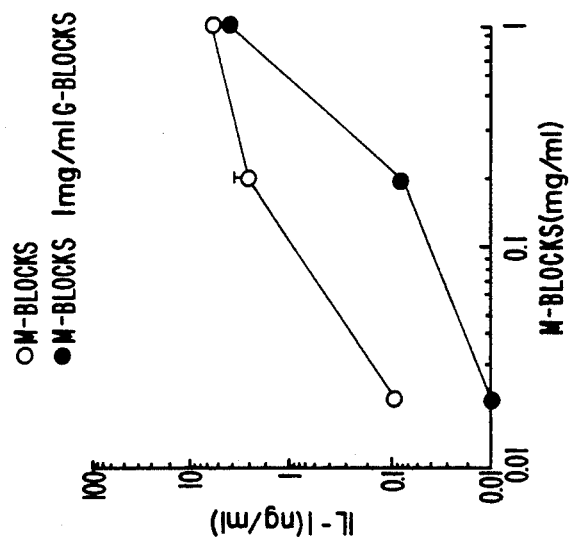
FIGS. 4a, 4b and 4c are graphs showing the inhibition of TNF-α (4a), IL-6 (4b) and IL-1 (4c) production from monocytes stimulated with M-blocks without (open square) and with addition of 1 mg/ml G-blocks (filled square). Production of cytokines from unstimulated monocytes and monocytes stimulated with 1 mg/ml G-blocks were less than 0.01 ng/ml.
Figure 4B:
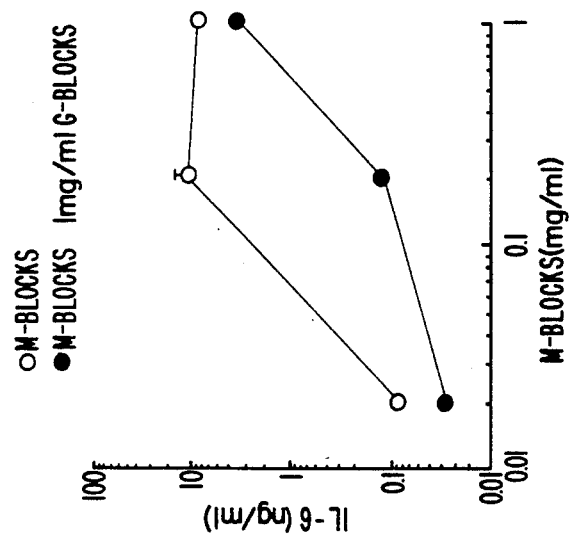
Figure 4A:
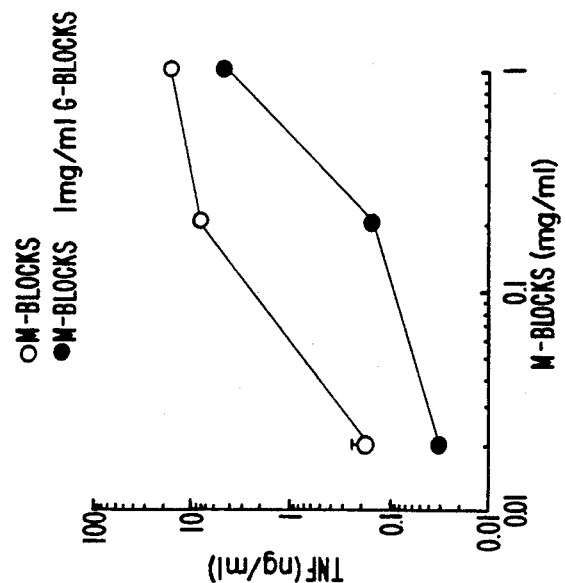

It was previously discovered by us that blocks of α1–4 L-GulA (G-blocks) in contrast to other poly uronic acids, do not stimulate monocytes to produce TNF-α, IL-1, or IL-6 (Otterlei M., Østgaar K., Skjåk-Braek G., Smidsrød O. and T. Espevik. 1991. Induction of cytokine production from human monocytes stimulated with alginate. J. Immunotherapy, In press). Thus, the question of whether G-blocks could inhibit the cytokine inducing capacity of M-blocks was examined. FIG. 4 *a, b,* and *c* demonstrate that addition of 1 mg/ml G-blocks to different concentrations of M-blocks inhibited the production of TNF-α, IL-6 and IL-1 from monocytes. The inhibition of cytokine production was more than 97% at a molar ratio of 5:1 for G- and M-blocks (FIG. 4 *a,b,c*).

Figure 2:
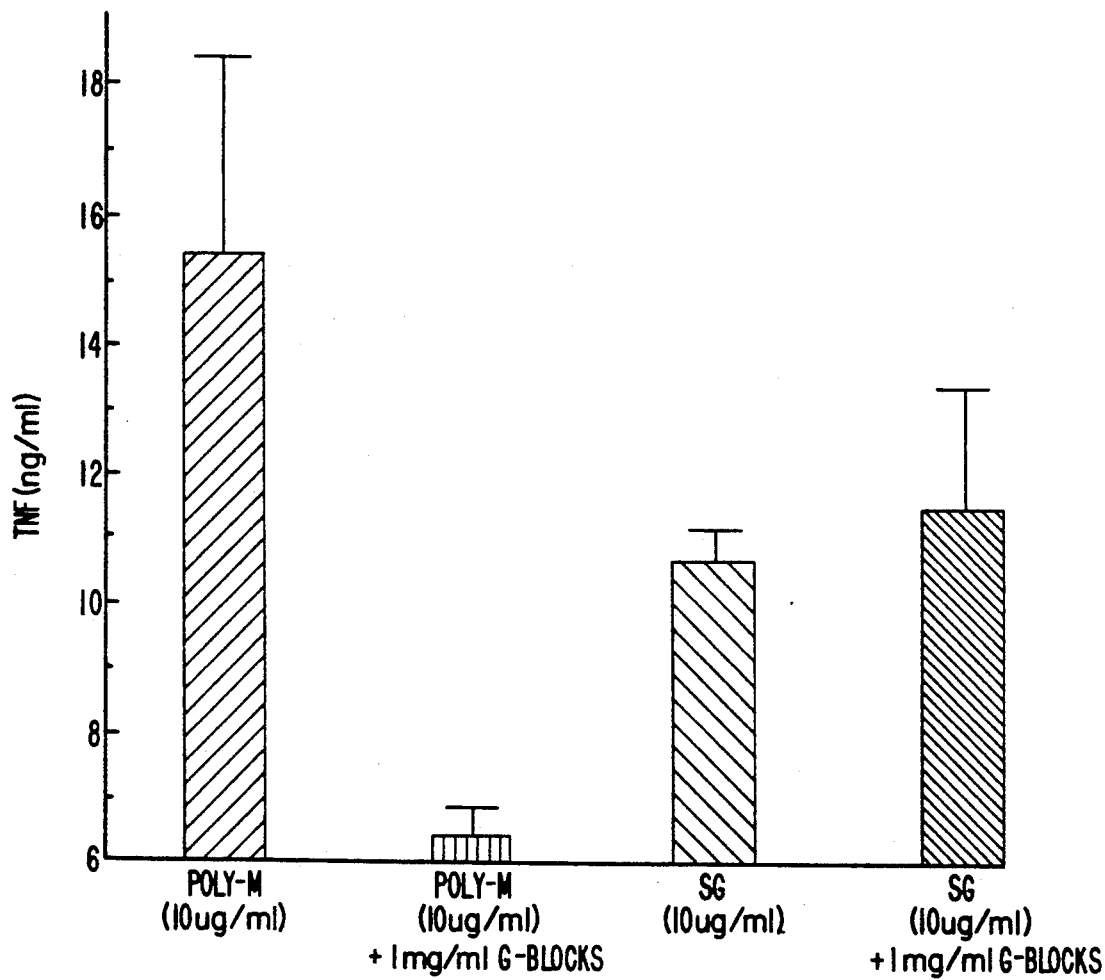
FIG. 2 is a bar graph showing the inhibition of TNF-α production from monocytes stimulated with Poly-M and SG with and without addition of G-blocks. Production of TNF-α from unstimulated monocytes and monocytes stimulated with 1 mg/ml G-blocks were less than 0.08 ng/ml.

Next the specificity of the G-block induced inhibition of TNF-α production was examined. Monocytes were stimulated with 10 μg/ml poly-M or SG in the presence or absence of 1 mg/ml G-blocks. As can be seen from FIG. 2 the G-blocks did not inhibit the TNF-α production induced by SG, while the poly-M induced TNF-α production was inhibited by 58%. This result shows that the inhibition in TNF-α production mediated by G-blocks is not due to unspecific toxicity. Furthermore, the G-blocks also inhibited the TNF-α production from C60XY stimulated monocytes by more than 90% (data not shown).

Figure 3:
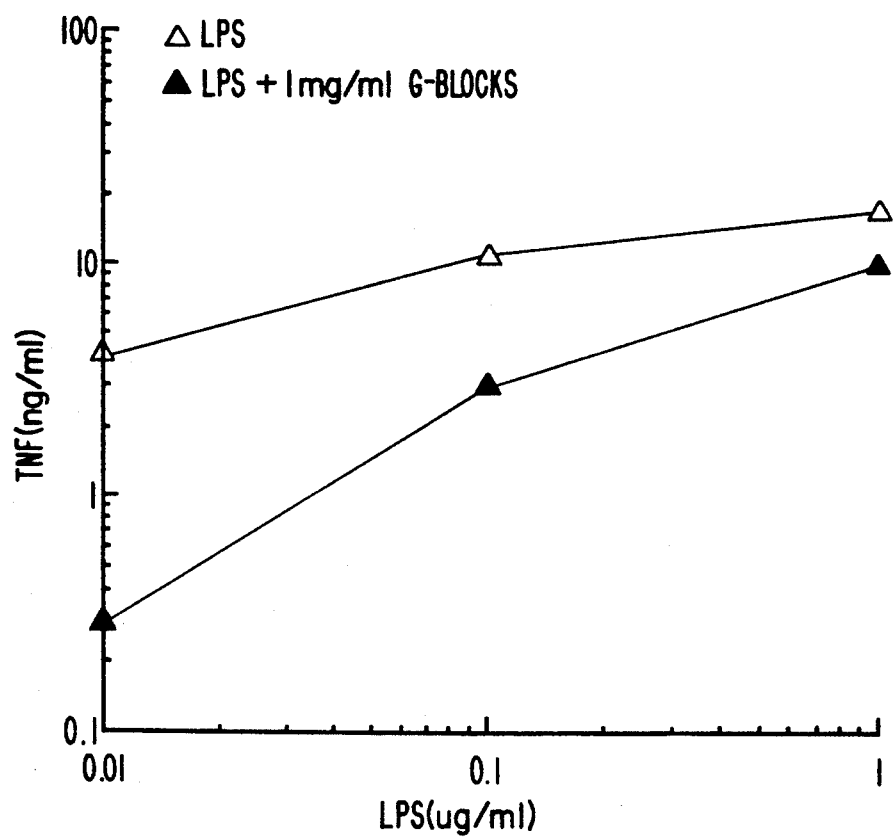
FIG. 3 is a graph showing TNF-α production from monocytes stimulated with LPS without (open triangle) and with addition of G-blocks (filled triangle). Production of TNF-α from unstimulated monocytes and monocytes stimulated with 1 mg/ml G-blocks were less than 0.1 ng/ml.

The LPS molecule contains a polysaccharide portion which is involved in its TNF-α stimulatory activity (Mannel D. N. and W. Falk. 1989. Optimal Induction of Tumor Necrosis Factor Production in Human Monocytes Requires Complete S-Form Lippopolysaccharide. Infection and Immunity, 57(7):1953). Consequently, the issue of whether G-blocks also could inhibit the TNF-a production from LPS stimulated monocytes was tested. FIG. 3 shows that addition of 1 mg/ml G-blocks to different concentrations of LPS reduces the TNF-α production by monocytes. The inhibition was more effective at lower concentrations of LPS reaching more than 90% at 0.01 μg/ml LPS. Thus, G-blocks are able to inhibit the TNF-α stimulatory activity of some polysaccharides and LPS.

Figure 5:
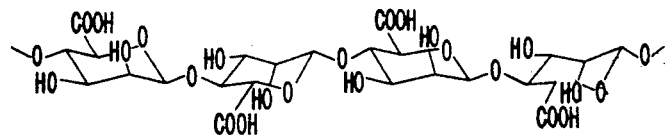
FIG. 5 is a schematic representation of a part of the structures of the different polysaccharides used in this study.
Figure 5:
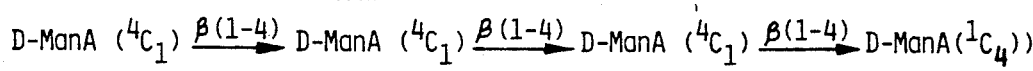
Figure 5:
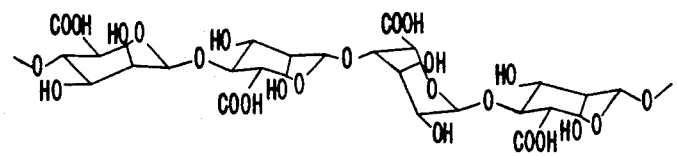
Figure 5:
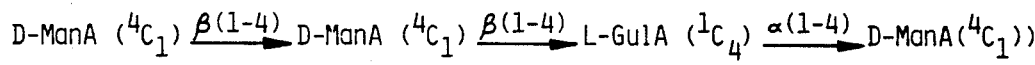
Figure 5:
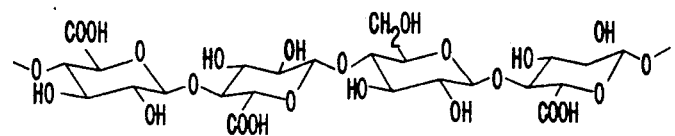
Figure 5:
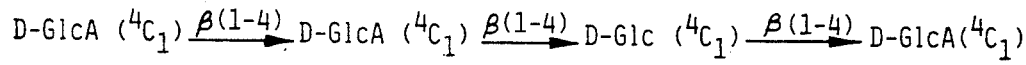
Figure 5:
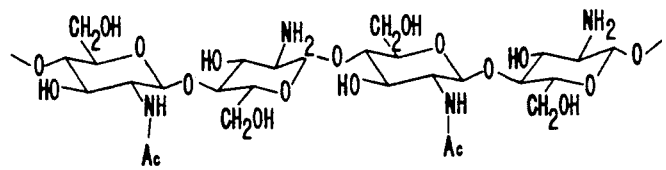
Figure 5:
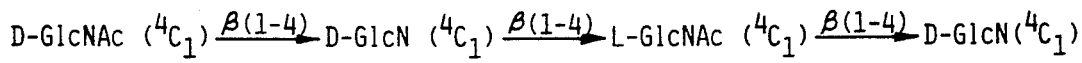
Figure 5:
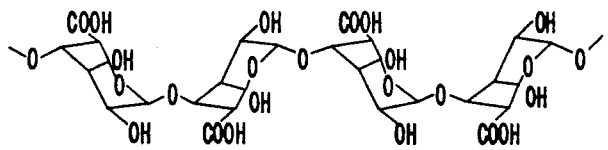
Figure 5:
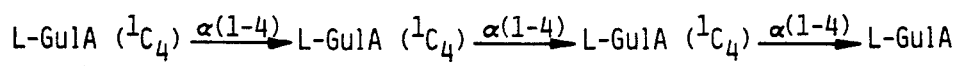

Interestingly, addition of G-blocks inhibited the cytokine production from monocytes stimulated with M-blocks, poly-M and C60XY, but not with SG. The G-blocks induced reduction in cytokine release was more pronounced at lower concentrations of M-blocks indicating a competitive inhibition. Without being bound to any particular theory, one possible explanation for the G-block induced inhibition of cytokines may be that poly-M, M-blocks, C60XY and G-blocks all bind to a common polysaccharide receptor on the monocyte surface. As previously discussed poly-M and C60XY have similar polysaccharide structure. Furthermore, the only structural difference between poly-M and M-blocks is the length of the homopolymeric D-ManA sequence (FIG. 5). In the M-blocks this sequence is broken up by L-GulA residues (5%) giving an average number of 5-7 consecutive D-ManA residues. Most of the glycosidic linkages in M-blocks are di-eq with a monomer length 5.17Å in the fully stretched form (Atkins E. D. T., Mackie E. E. and F. E. Smolko. 1970. Crystalline structure of alginic acid. Nature 225:626), but when a D-ManA is linked to a L-GulA instead of D-ManA the glycosidic linkage is a equatorial-axial (eq-ax) nature (FIG. 5). The length between the monomers in a eq-ax binding is shorter than in a di-eq binding. Since D-ManA and L-GulA have almost identical structures (different only in the configuration around C-5) the large difference between M- and G-blocks ability to stimulate cytokine production must be due to the difference in the conformation they adapt as part of a homopolymeric structure (FIG. 5).

The G-blocks have mainly di-axially (di-ax) glycosidic linkages which are even shorter (4.36Å) than the eq-ax binding (Atkins E. D. T., Mackie E. E. and F. E. Smolko. 1970. Crystalline structure of alginic acid. Nature 225:626). G-blocks will also contain some ax-eq linkages between L-GulA and D-ManA (10%). The G-blocks are more compact than M-blocks, C60XY and poly-M but the chains have all two folded screw axis in the solid state and statistical mechanical calculations has shown that this linkage conformation is also highly populated in solutions (Smidsrod O., Haug A. and S. Whittington. 1972. The molecular basis for some physical properties of polyuronides. Acta. Chem. Scand. 26:2563; Smidsrod O., Glover R. M. and S. G. Whittington. 1973. The relative extension of alginates having different chemical compositions. Carbohydr. Res. 27:107).

Based on the examination of the polysaccharide structures it is possible that the M-blocks, poly-M and G-blocks bind to a common polysaccharide receptor on monocytes. This conclusion is strengthened by binding data showing that G-blocks are able to inhibit binding of poly-M to monocytes (See FIG. 6). The reason why G-blocks did not inhibit SG induced TNF-α production could be due to the structure of this polysaccharide. The SG (β1-3 linked D-Glc) has a triple helix structure at m.w. above 50,000 with a repeat unit, containing 6 residues of 1.8 mm, along the axes (Kojima T., Tabata K., Itoh W. and T. Yanaki. 1986. Molecular Weight Dependence of the Antitumor Activity of Scizophyllan. Agric. Biol. Chem., 50(1):231; Bluhm T. L., Deslaudes I., Marchesean R. T., Perez S. and M. Rinando. 1982. Solid state and solution conformation of scleroglucan. Carbohydr. Res. 1:117). SG will consequently have different 3D structure from the β1-4 and α1-4 linked polysaccharides, and consequently may not bind to the same receptor.

Figure 6A:
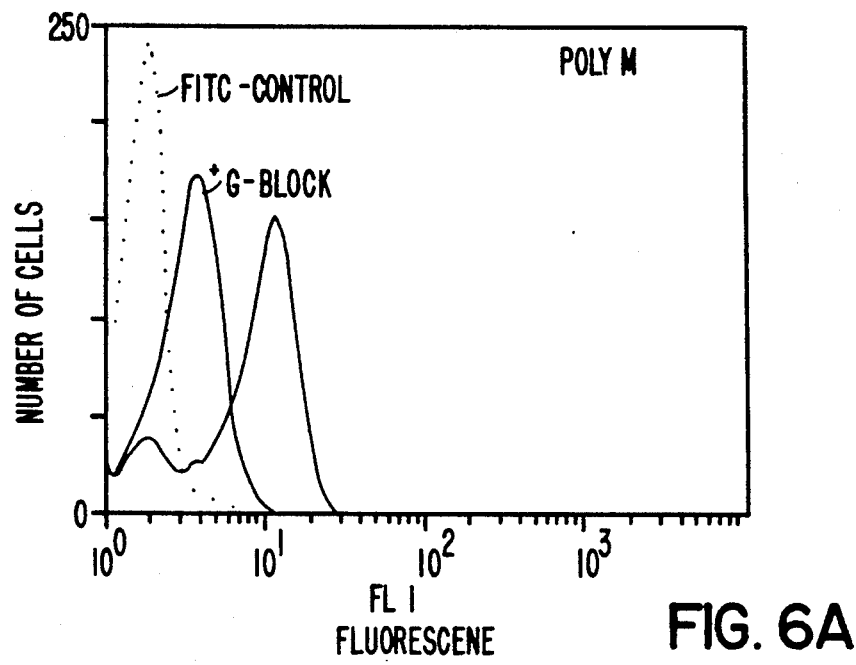
FIGS. 6A and 6B are graphs showing flow cytometry histograms of poly-M binding to monocytes in the presence of excess of G-blocks (6A) and LPS (6B). Binding of poly-M was quantitated by using a FITC-labeled monoclonal antibody (2G8, developed by us) which is specific for poly-M. Increased fluroescence represents increased poly-M binding to monocytes.
Figure 6B:
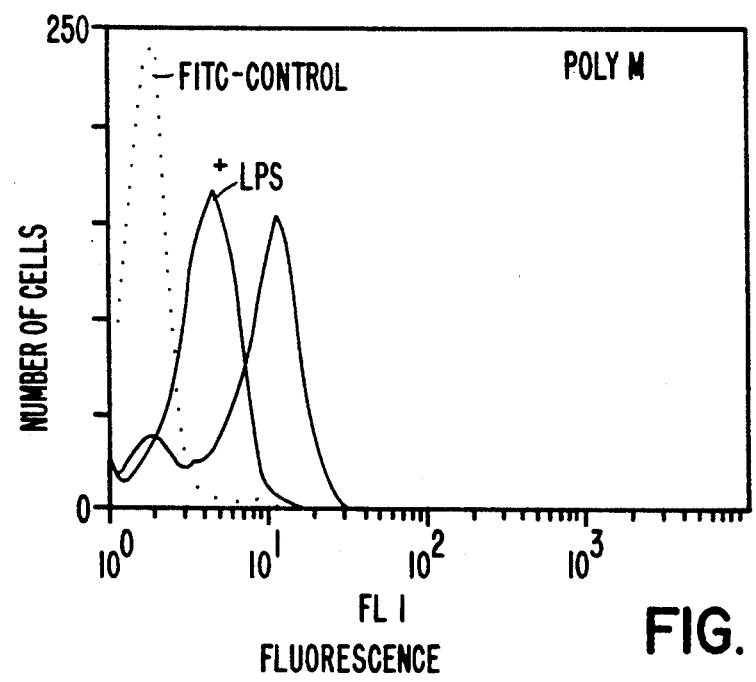
Figure 1:
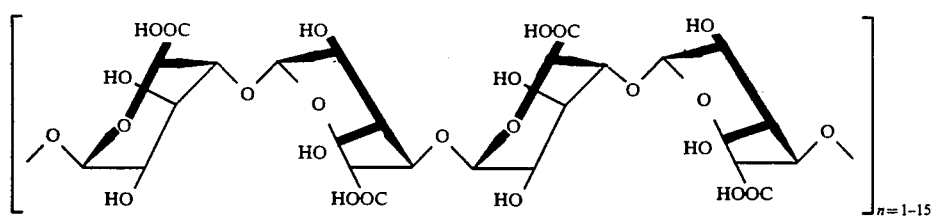

It was also observed that G-blocks inhibited the LPS induced TNF-α production from monocytes. One possible explanation for this effect is that the polysaccharide part of LPS is essential for binding of LPS to monocytes, and that the polysaccharide part has similarities with G-blocks. The indication that LPS and G-blocks share a common receptor is further verified by measuring binding of poly-M to monocytes. These binding experiments indicate that LPS and G-blocks inhibits the binding of poly-M to monocytes (FIG. 6). TNF-α has been shown to be a mediator of septic shock caused by Gram negative infections (Exley A. R., Cohen J., Buurman W., Lumley J., Hanson G., Aulalih J. M., Bodmer M., Stephens S., Riddel A. and M. Perry. 1990. Monoclonal antibody to TNF-α in severe septic shock. Lancet 335:1275; Waage A., Halstensen A. and T. Espevik. 1987. Association between tumor necrosis factor in serum and fatal outcome in patients with meningococcal Lancet i:355). Consequently, the identification of a defined polysaccharide which inhibits the TNF-α inducing capacity of LPS may have important implications for treatment of Gram negative septic shock.

TABLE 1

| POLY-SACCHARIDE | LINKAGE | MW/DP$_n$ | MONOMER COMPOSITION |
|---|---|---|---|
| Poly-M | β1-4 | [1],[2]270,000 (M$_w$) | 100% D-mannuronic acid |
| M-blocks | β1-4 | DP$_n$ = 30-35 | 95% D-mannuronic acid, 5% L-guluronic acid |
| C6OXY | β1-4 | 60,000 (M$_w$) | 94% D-glucuronic acid, 6% D-glucose |
| Chitosan | β1-4 | [1]100,000 (M$_n$) | 60% N-acetylglucosamine 40% N-glucosamine |
| G-blocks | α1-4 | DP$_n$ = 25-30 | 90% L-guluronic acid 10% D-mannuronic acid |
| SG | β1-3 | 384,000 (M$_w$) | 100% D-glucose |

[1]Samples used in FIG. 1Samples used in FIG. 3

What is claimed is:

1. A method of treating a human to inhibit tissue injury accompanying inflammation resulting from leukocyte activity induced by cytokines produced in response to an inflammatory stimulus in the human, wherein the method comprises administering to said human oligomers or polymers of L-guluronic acid, wherein said oligomers or polymers of L-guluronic acid are administered to said human in an amount sufficient to inhibit the production of human interleukin-1, human interleukin-6, human tumor necrosis factor, and other human leukocyte-derived human cytokines in said human to thereby inhibit said tissue injury.

2. The method of claim 1 wherein said oligomers or polymers of L-guluronic acid comprise α1-4 linked L-guluronic acid.

3. The method of claim 2 wherein said oligomers or polymers of L-guluronic acid comprise 90% L-guluronic acid and 10% D-mannuronic acid and have a DP$_n$=10-60.

4. A method of treating a human to inhibit tissue injury accompanying inflammation resulting from leukocyte activity induced by cytokines produced in response to an inflammatory stimulus in the human, wherein the method comprises administering to said human a composition comprising oligomers or polymers of α1-4 linked L-guluronic acid, wherein said oligomers or polymers of α1-4 linked L-guluronic acid is administered to said human in an amount sufficient to modulate the inflammatory effect of human interleukin-1, interleukin-6 and human tumor necrosis factor, and other human leukocyte-derived cytokines in said human to thereby inhibit said tissue injury.

5. The method of claim 4 wherein said oligomers or polymers of L-guluronic acid residues comprise 90% L-guluronic acid and 10% D-mannuronic acid residues and have a DP$_n$=10-60.

6. A method of treating a mammal to inhibit tissue injury accompanying inflammation resulting from leukocyte activity induced by cytokines produced in response to an inflammatory stimulus in the mammal, wherein the method comprises administering to said human an effective amount of oligomers or polymers of α1-4 linked L-guluronic acid wherein said α1-4 linked L-guluronic acid are administered to said human in an amount sufficient to inhibit the stimulatory effect of leukocyte-derived cytokines to thereby inhibit said tissue injury.

7. The method of claim 6 wherein said oligomers or polymers of α1-4 linked -guluronic acid comprise 90% L-guluronic acid and have a DP$_n$=10-60.

8. The method of claim 6 wherein said oligomers or polymers of α1-4 linked L-guluronic acid comprises di-axially linked uronic acid polymers of glucouronan with a repeat distance of about 4.36Å.

9. A method of treating a human to alleviate inflammatory pathological effects of sepsis, septic shock, endotoxic shock, gramnegative sepsis, and toxic shock syndrome, wherein the method comprises administering to said human oligomers or polymers of α1-4 linked L-guluronic acid, wherein said α1-4 linked L-guluronic acid are administered to said human in an amount sufficient to inhibit production of human interleukin-1, interleukin-6, human tumor necrosis factor, and other human leukocyte-derived human cytokines on polymorphonuclear leukocytes or monocytes in said human to thereby inhibit said effects.

10. The method of claim 9 wherein said oligomers or polymers of α1-4 linked L-guluronic acid comprise 90% L-guluronic acid and have a DP$_n$=10-60.

11. A method of treating a human to inhibit tissue injury accompanying inflammation resulting from leukocyte activity induced by cytokines produced in response to an inflammatory stimulus in the mammal, wherein the method comprises administering to said human an effective amount of a compound shown in FIG. 1 below:

wherein said compound is administered to said human in an amount sufficient to inhibit the stimulatory effect of leukocyte-dervied cytokines to thereby inhibit said tissue injury.

* * * * *

UNITED STATES PATENT AND TRADEMARK OFFICE
CERTIFICATE OF CORRECTION

PATENT NO. : 5,166,137
DATED : November 24, 1992
INVENTOR(S) : Otterlei, et al.

It is certified that error appears in the above-identified patent and that said Letters Patent is hereby corrected as shown below:

In Column 10, at line 40, change

"linked - guluronic"  to  -- linked L-guluronic --

Signed and Sealed this

Twenty-first Day of March, 1995

Attest:

BRUCE LEHMAN

Attesting Officer       Commissioner of Patents and Trademarks